US006403605B1

(12) United States Patent
Heaton et al.

(10) Patent No.: US 6,403,605 B1
(45) Date of Patent: Jun. 11, 2002

(54) METHODS FOR THE NORMALIZATION OF SEXUAL RESPONSE AND AMELIORATION OF LONG TERM GENITAL TISSUE DEGRADATION

(75) Inventors: Jeremy P. W. Heaton; Michael A. Adams, both of Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/086,630

(22) Filed: May 29, 1998

(51) Int. Cl.$^7$ .............................................. A61K 31/44

(52) U.S. Cl. ..................................................... 514/284

(58) Field of Search .............................. 514/926, 772.6, 514/356, 309, 254, 280, 284, 267; 544/200, 251; 424/430, 435, 464, 260, 258, 251; 546/926, 75, 48; 128/78, 79, 214–215

(56) References Cited

U.S. PATENT DOCUMENTS

| | | | | |
|---|---|---|---|---|
| 2,818,855 A | 1/1958 | Miller | .......................... | 128/79 |
| 4,127,118 A | 11/1978 | Latorre | .......................... | 128/79 |
| 4,521,421 A | 6/1985 | Foreman | ...................... | 514/267 |
| 4,543,256 A | 9/1985 | Neumeyer | ................... | 514/280 |
| 4,687,773 A | 8/1987 | Neumeyer et al. | ........... | 514/280 |
| 4,727,064 A | 2/1988 | Pitha | ........................... | 514/58 |
| 4,801,587 A | 1/1989 | Voss et al. | ................... | 514/248 |
| 5,242,391 A | 9/1993 | Place et al. | .................... | 604/60 |
| 5,270,323 A | 12/1993 | Milne, Jr. et al. | ............. | 514/309 |

FOREIGN PATENT DOCUMENTS

| | | | | |
|---|---|---|---|---|
| EP | 0 579 435 A1 | 1/1994 | .......... | A61K/47/48 |
| EP | 0 714 663 A2 | 6/1996 | .......... | A61K/45/06 |
| WO | WO 87/04621 | 8/1987 | .......... | A61K/31/50 |
| WO | 94/22445 | 10/1994 | .......... | A61K/31/48 |
| WO | WO 95/28930 | 11/1995 | .......... | A61K/31/485 |
| WO | WO 97/137710 | 4/1997 | .......... | A61K/31/46 |

OTHER PUBLICATIONS

Harrison's Principles of Internal Medicine, Ninth Edition,: "Section 8: Alterations in Reproductive and Sexual Function—Sub–Section 47: Disturbances of Sexual Function and Reproduction in Men", eds.: Isselbacher et al., New York: McGraw–Hill Book Compa.*
Segraves, "Effects of Psychotrophic Drugs on Human Erection and Ejaculation," Arch. Gen. Psychiatry, vol. 46, <arch 1989, pp. 275–284.*
Samarthji Lal, et al., Apomorphine–Induced Penile Tumescence in Impotent Patients–Preliminary Findings, 1987 *Prog. Neuro–Pshychoparmacol & Biol. Psychiat.*, vol., II, pp. 235–242.
Jeremy P. W. Heaton, M.D., et al., Recovery of Erectile Function by the Oral Administration of Apomorphine, Feb. 1995, *Urology*, vol. 45, No. 2, pp. 200–206.

I. Goldstein and JR Berman, Vasculogenic Female Sexual Dysfuction: Vaginal Engorgement and Clitoral Erectile Insufficiency Syndromes, *International Journal of Impotence Research* (1998) 10, Suppl 2, pp. S84–S90.
R.T. Segraves, Editorial: Pharmacological Era in the Treatment of Sexual Disorders, (1998) *Journal of Sex & Marital Therapy*, vol. 24, pp. 67–68.
Tagliamonte et al., Pharm. Biochem. and Behavior vol. 2, pp. 257–260 (1974).
Laduron et al., Biochem. Pharmacology, vol. 28, pp. 2161–2165 (1979).
Baldessarini et al., in Gessa et al., eds., Apomorphine & Other Dopaminomimetics, vol. 1, Basic Pharmacology, pp. 219–288 (1981).
Lal et al., J. Neural Transmission, vol. 54, pp. 75–84 (1982).
Reynolds, James E. F., ed., Martindale, 28th Edition, pp. 891–892 (1982).
Gower et al., European J. of Pharmacology, vol. 122, pp. 239–244 (1986).
Melis et al., Brain Research, vol. 415, 98–104 (1987).
Segraves et al., Archives of Sexual Behavior, vol. 16, No. 2, pp. 125–137 (1987).
Danjou et al., Br.J. Clin. Pharmac., vol. 26, pp. 733–739 (1988).
Lal S., Prog. Neuro–Psychopharm. & Biol. Psych., vol. 12, pp. 117–164 (1988).
Pehek et al., Pharm. Biochem. and Behavior 31:201–208 (1988).

(List continued on next page.)

*Primary Examiner*—Bennett Celsa
*Assistant Examiner*—Tomas Friend
(74) *Attorney, Agent, or Firm*—Jerry F. Janssen; Carol Miernicki Steeg; Stephen J. Scribner

(57) ABSTRACT

The present invention provides, in one embodiment, a method of normalizing the timing of sexual response in a mammal comprising the administration of an amount of a central nervous system sexual response initiator in an amount sufficient to produce genital vasodilation but less than the amount required to produce effective vasocongestive arousal.

Figure 1:
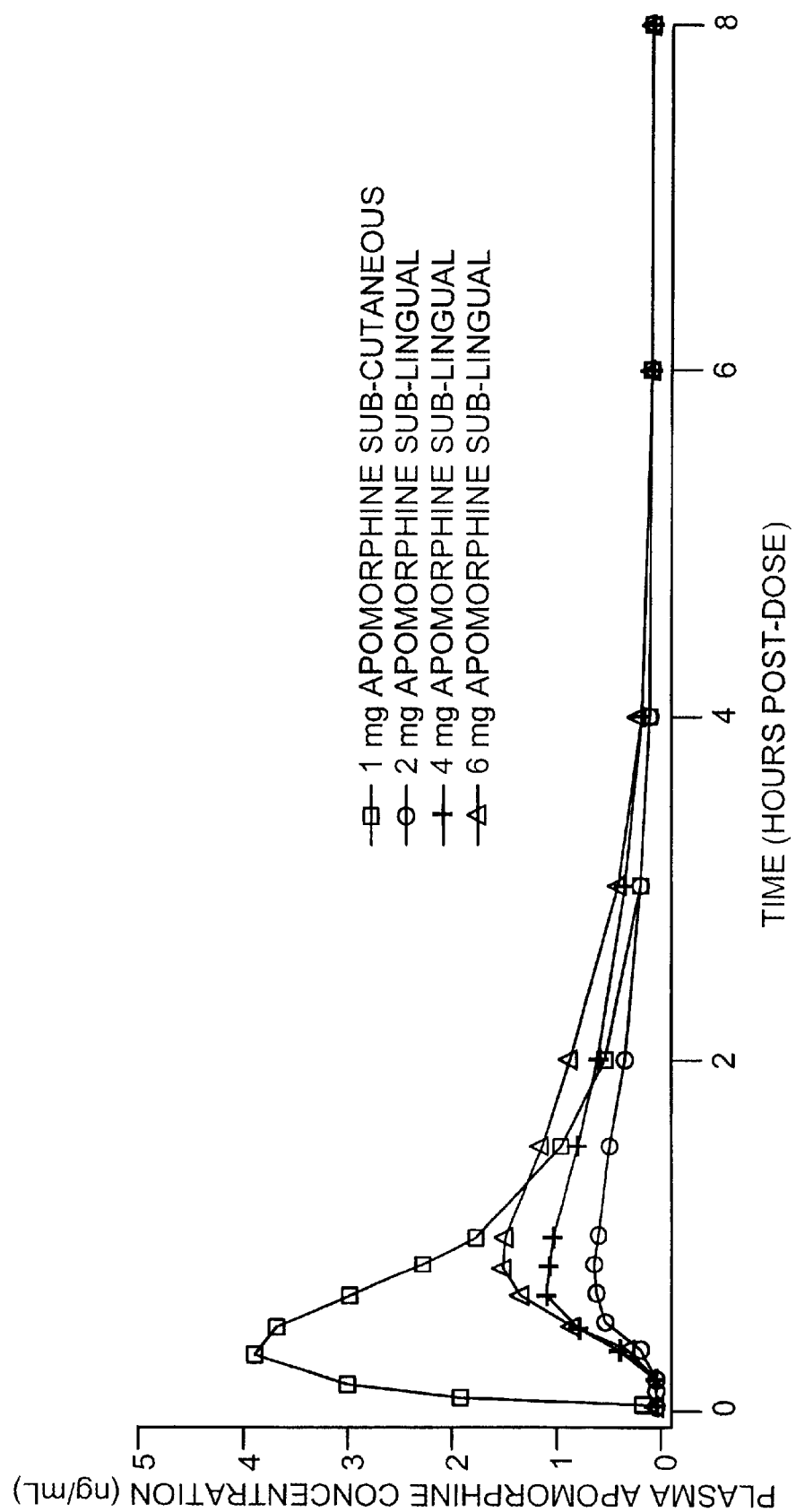

The method is applicable not only to adjusting or normalizing the timing of sexual response in humans, but in the breeding of valuable commercial animals such as horses, cattle, sheep, swine and the like and domesticated pets such as dogs and go cats.

In an alternative embodiment, the present invention provides a method for the prophylactic treatment of long-term tissue degradation in the genital organs comprising the administration to a mammal of a central nervous system sexual response initiator in an amount sufficient to produce genital vasodilation but less than the amount required to produce effective vasocongestive arousal.

The preferred central nervous system sexual response initiator is apomorphine or a pharmaceutically acceptable acid addition salt thereof.

11 Claims, 1 Drawing Sheet

OTHER PUBLICATIONS

Danjou et al., J. Pharamacol. Methods, vol. 21, pp. 61–69 (1989).

Gancher et al., AM. Neurol., vol. 26, pp. 232–238 (1989).

Segraves R. T., Arch. Gen. Psych., vol. 46, pp. 275–284 (1989).

Durif et al., Eur. J. Clin. Pharmacology, vol. 41, pp. 493–494 (1991).

Essink et al., J. Chromatography, vol., 570, pp. 419–424 (1991).

Gancher et al., Movement Disorders, vol. 6, No. 3, pp. 212–216 (1991).

Heaton et al., J. Urology, vol. 145, pp. 192–194 (1991).

Heaton et al., J. Urology, vol. 145, pp. 1099–1102 (1991).

Lal et al., J. Psych. Neurosci., vol. 16, No. 5, pp. 262–266 (1991).

Montastruc et al., Clin. Neuropharmacology, vol. 14, No. 5, pp. 432–437 (1991).

Panegyres et al., Med. J. Australia, vol. 155, pp. 371–374 (1991).

Segraves et al., J. Urology, vol. 145, pp. 1174–1175 (1991).

Durif et al., Clinical Neuropharmacology, vol. 16, No. 2, pp. 157–166 (1993).

Heaton et al., J. Urology, vol. 151, pp. 797–800 (1994).

Bancroft, J., editor, The Pharmacology of Sexual Function and Dysfunction, pp. 225–229 (1995).

Goodman and Gilman, eds., The Pharmacological Basis of Therapeutics, 9th Edition, pp. 4–9 (1996).

* cited by examiner

METHODS FOR THE NORMALIZATION OF SEXUAL RESPONSE AND AMELIORATION OF LONG TERM GENITAL TISSUE DEGRADATION

TECHNICAL FIELD

The present application relates to pharmaceutical formulations and to medical methods of treatment. More particularly, the present invention concerns the use of a compound which acts as a central nervous system sexual response initiator for the normalization of the timing of sexual response in humans and for the prophylaxis or treatment of long-term damage to genital organ.

BACKGROUND OF THE INVENTION

Proper sexual functioning in men and women depends upon a combination of steps including 1) establishment of the appropriate anticipatory mental set ("desire"), 2) effective vasocongestive arousal (an erection in the male sufficient for vaginal penetration and, in the female, clitoral erection, vaginal engorgement and lubrication), and 3) orgasm. The timing of these steps between partners engaging in sexual relations is mediated by one or more of several compounds which act in neurological pathways in the mesencephalon or mid-brain. These pathways include those termed the serotonergic, dopaminergic, oxytocinergic, and nitroxidergic mid-brain pathways. Timing of the various aspects or parameters of sexual response between partners engaging in sex is important and often mis-matched due to psychological, or sometimes biogenic, dysfunction in one or both of the partners. Even in sex partners having sexual responses deemed to fall within the norm, there is a frequent mis-match of the timing of response.

Orgasm in the male includes the sensation of emission followed by ejaculation. The sensation of emission is one of ejaculatory inevitability and is mediated by contractions of the prostate, seminal vesicles, and urethra. Orgasm in the female is accompanied by contractions of the muscles that line the wall of the outer third of the vagina. In both sexes, generalized muscular tension, perineal contractions and involuntary pelvic thrusting usually occur. Orgasm is followed by resolution, a sense of general relaxation, well-being, and muscular relaxation. During this phase men are physiologically refractory to further erection and orgasm for a variable period of time. In contrast, women may be able to respond to additional stimulation almost immediately.

Sexual response is mediated by a balanced interplay between the sympathetic and parasympathetic nervous systems. Vasocongestion, or erectile tumescence, is largely mediated by parasympathetic (cholinergic) outflow, whereas orgasm is predominantly sympathetic (adrenergic). Ejaculation is almost entirely sympathetic, whereas emission involves a much more finely balanced combination of sympathetic and parasympathetic stimulation.

Normal biological response in humans results in ejaculation typically within about two minutes or more following vaginal penetration. Most women are unable to reach orgasm within this short period of time, one cause of the problem of inappropriate timing of sexual response between sexual partners, even when the sexual responses of both are within physiological norms. In the case of the sexual dysfunction in males known as premature ejaculation, the problem is further exacerbated.

Premature ejaculation in males may have either a psychogenic or biogenic origin in a particular individual, and various treatment methods have been suggested. These include counseling and techniques for learning control of ejaculation and the use of serotonin re-uptake inhibitors such as fluoxetine hydrochloride (Prozac®) and sertraline hydrochloride (Zoloft®) to delay the onset of the sensation of emission.

The problem of inappropriate timing of sexual response is not limited to the human species, but occurs also in lower mammals as well, for example, in the breeding of valuable commercial animals such as horses, cattle, sheep, swine and the like and domesticated pets such as dogs and cats.

U.S. Pat. No. 5,770,606 (Ser. No. 08/546,498) discloses a method of ameliorating erectile dysfunction in a male patient by administration of apomorphine or a salt thereof in an amount sufficient to induce an erection adequate for vaginal penetration, but less than that which induces nausea.

The need remains, however, for the development of effective means to normalize the timing of sexual response in mammals, including humans and, in particular, in those cases involving premature ejaculation in human males.

In addition, there is a need for agents for the prophylaxis and treatment of long-term degradative effects or damage to genital organ tissues in mammals.

BRIEF DESCRIPTION OF THE DRAWING FIGURE

FIG. 1 is a linear plot of the mean plasma concentrations of apomorphine following the administration of subcutaneous and sublingual doses of apomorphine.

SUMMARY OF THE INVENTION

It has been found, in accordance with one embodiment of the present invention that the acute administration of an agent which acts upon mid-brain dopaminergic, serotonergic, oxytocinergic or nitroxidergic pathways to initiate mammalian sexual response in an amount which is insufficient to produce effective vasocongestive arousal, but is sufficient to produce increased genital vasodilation, acts to normalize the timing of sexual response between sexual partners.

In another embodiment, the present invention provides a method of ameliorating long-term genital organ tissue damage comprising the chronic administration of a mammalian central nervous system sexual response initiator in an amount less than that required to produce a vasocongestive arousal in said mammal, but sufficient to cause vasodilation in the genitalia.

DETAILED DESCRIPTION

In the first embodiment of the invention, a central nervous system sexual response initiator is administered to a mammal in an acute dose to one or both partners in the period just prior to sexual intercourse, preferably in a dose insufficient to cause effective vasocongestive arousal, but sufficient to increase genital vasodilation to aid in the normalization of the timing of sexual response between the sexual partners. The drug is administered during the period between about two to about one-hundred-twenty minutes prior to sexual relations, preferably in the period between about two and sixty minutes prior to sexual relations.

In the case where the male suffers from the sexual dysfunction termed sexual arousal disorder (inability to attain the psychic readiness, and/or sustain an erection satisfactory for normal coitus) or the condition known as premature ejaculation, the drug is administered to the male partner. Where the female suffers sexual arousal disorder (persistent or recurrent failure to attain the psychic readiness and/or maintain the lubrication-swelling response), the drug is administered to the female partner. In the case of both the male and female partners, the drug may also be co-administered with a low dose of androgen to potentiate the effect of the mid-brain pathway mediator drug.

By "androgen" is meant testosterone, dihydrotestosterone, and dehydroepiandrostenedione, either in their free base forms or in the form of a salt or pro-drug.

The terms "acute dose" or "acute administration" of the drug mean the scheduled administration of the drug to the patient on an as-needed basis.

The term "central nervous system sexual response initiator" denotes a compound which acts in any of the dopaminergic, serotonergic, oxytocinergic or nitroxidergic mammalian mid-brain pathways to initiate a sexual response.

Dopaminergic pathway initiators include apomorphine, bromocriptine, lisuride, methergoline, pergolide, piribidil, and quinpirole.

Serotonergic pathway initiators include serotonin receptor agonists such as 1-(2,5-dimethoxy-4-iodophenyl)-1-aminopropane, 5-methoxytryptamine, α-methyl-5-hydroxytryptamine, 2-methyl-5-hydroxytryptamine, N-acetyl-5-hydroxytryptamine buspirone, and sumatriptin.

Oxytocinergic pathway initiators include oxytocin analogues such as isotocin, carbetocin, Lys-conopressin, deaminooxytocin, mesotocin, antocin, glumitocin, aspargitocin, valitocin, asvatocin, phasvatocin, and seritocin.

The preferred central nervous system sexual response initiator for use in the methods of the present invention is apomorphine or one of its salts or pro-drug forms.

Apomorphine, (R)-5,6,6a,7-tetrahydro-6-methyl-(4H)-dibenzo[de,g]quinoline-10,11-diol, is a derivative of morphine obtained by treatment of the latter with concentrated hydrochloric acid (L. Small, et al., *J. Org. Chem.*, 5: 334 (1940)) or by heating morphine with zinc gchloride (Mayer, Ber., 4: 171 (1871)). The compound has the chemical structure:

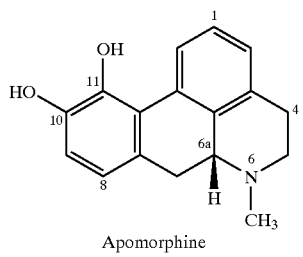

Apomorphine and possesses a chiral center at position 6a. The total synthesis of the racemic mixture is reported by J. L. Neumeyer, et al., *J. Pharm. Sci.*, 59:1850 (1970) and the synthesis of the separate enantiomers by V. J. Ram and J. L. Neumeyer, *J. Orq. Chem.*, 46: 2830 (1981).

The compound possesses a basic nitrogen atom at position 6 and is thus capable of existing in the free base form as well as acid addition salt forms. The compound may be administered as the free base or in the form of one of its pharmaceutically acceptable salts or pro-drug derivatives.

As used herein, the term "pharmaceutically acceptable salt" refers to those salts which are within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977). The salts are prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

The term "pro-drug" refers to compounds that are rapidly transformed in vivo to yield the parent compound, as for example, by hydrolysis in blood. T. Higuchi and V. Stella provide a thorough discussion of the pro-drug concept in "Pro-drugs as Novel Delivery Systems", Vol. 14 of the A.C.S. Symposium Series, American Chemical Society (1975). Examples of esters useful as pro-drugs for compounds containing carboxyl groups may be found on pages 14–21 of "Bioreversible Carriers in Drug Design: Theory and Application," edited by E. B. Roche, Pergamon Press (1987).

The term "pro-drug ester group" refers to any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butryates, acrylates and ethylsuccinates.

By the term "normalizing" or "normalization" of the timing of sexual response in a human is meant adjusting the time of onset, duration, and likelihood of a sexual response so that these parameters tend toward the normal response for a human under the given circumstances. Normalization of sexual response can include delay of onset of the sensation of emission, delay of ejaculation, and prolongation of the duration of erection in the male and, in the female, increase in the likelihood of clitoral erection, swelling and lubrication.

The term "premature ejaculation" in the male is meant the sexual dysfunction characterized by persistent or recurrent ejaculation before, upon, or shortly after vaginal penetration. More generally, the term can be defined as ejaculation occurring before the individual wishes.

The term "vasocongestive arousal" means, in the male, tumescent penile erection, but insufficient for vaginal penetration and, in the female, clitoral erection and engorgement and swelling of the vagina and labia. The term "effective vasocongestive arousal" means, in the male, an erection sufficient for vaginal penetration.

The following study illustrates the use of apomorphine, a representative drug of the class of compounds contemplated by the present invention, for normalizing the timing of sexual response by administration of the drug to males to extend the duration of erection.

A multi-center, double-blind, randomized, placebo-controlled, three-armed study was conducted on 370 patients diagnosed with male erectile dysfunction with no major organic component. For each sequence, patients received placebo in one of the treatment periods, and a dose (2 mg, 4 mg, or 6 mg) of apomorphine in the other treatment period. This arrangement resulted in approximately one-third of the patients receiving one of the three apomorphine doses.

During treatment periods of the study, patients and their sexual partners were instructed to attempt intercourse a minimum of twice weekly. Each time the study drug was taken, a questionnaire was completed by the patient and by the partner and mailed to the study sponsor. The questionnaire recorded the date and time the study drug was taken, an evaluation of the erection, whether or not sexual intercourse had occurred, and satisfaction associated with each attempt. The patient also completed a diary which recorded the latency and duration of erections associated with the use of the study drug and antiemetic and concomitant medication usage and any adverse effects. If an erection occurred after administration to the patient of the study drug, the duration of erection and time-to-erection were recorded in the patient diary. The data from these studies are presented in Tables 1–4.

Table 1 shows the mean durations in minutes of erections for patients receiving a dose (2 mg, 4 mg, or 6 mg) of apomorphine versus placebo in each case for all attempts. If the attempt failed to produce an erection, a value of zero minutes was used in the statistical analysis. The data in Table 1 indicate dose-dependent, statistically significant differences in the mean durations of erections between drug and placebo, with the mean values being lowered by overall by inclusion of zero value data from attempts which did not result in an erection.

Table 2 shows the data for only those attempts which did result in an erection. The data in Table 2 also indicate a dose-dependent, statistically significant difference of duration of erection, with a difference of almost 5 minutes between patients taking the 6 mg dose and those receiving placebo.

Table 3 presents the median time to erection for patients involved in the study and shows data for all attempts. In those cases where no erection was achieved, a value of 60 minutes time-to-erection was used in the statistical analysis. The data in Table 3 show differences in latency periods between patients receiving apomorphine and those receiving placebo, but the differences probably reflect the inclusion in the data of 60 minute values for those cases in which no erection was achieved.

Table 4 shows the data only for patients where an attempt was successful in achieving an erection. The data in Table 4 show that there was no statistically significant difference in the median time-to-erection between patients receiving the drug and those receiving placebo, with a median time-to-erection of about 12 minutes.

One conclusion to be drawn from the data presented in Tables 1–4 is that administration of apomorphine at the doses tested did not shorten or prolong the time of onset of erection despite effects on the duration of erection when compared to placebo, but resulted in a significant increase in the duration of erection. Keeping in mind the generally longer time typically required for females to reach orgasm in the cycle of sexual response, administration of the drug to the male partner serves to normalize the timing of sexual response between coital partners.

The data in Tables 3 and 4 are instructive in another light. The median time-to-erection in patients receiving the study drug at all doses tested was approximately 12 minutes. However, a pharmacokinetic evaluation of apomorphine,

TABLE 1

Duration of Erection
Results of Statistical Analysis of Average Durations
Based on All Attempts

| Study Arm | Treatment | Number of Patients | Mean (Minutes) | Difference in Means (Minutes) | Standard Error of the Mean | P-Value |
|---|---|---|---|---|---|---|
| Apomorphine 6 mg | Drug | 111 | 8.393 | 5.138 | 0.883 | <0.001[1] |
| | Placebo | 111 | 3.255 | | | |
| Apomorphine 4 mg | Drug | 129 | 6.903 | 3.578 | 0.637 | <0.001[1] |
| | Placebo | 129 | 3.325 | | | |
| Apomorphine 2 mg | Drug | 135 | 5.020 | 1.936 | 0.534 | <0.001[1] |
| | Placebo | 135 | 3.084 | | | |

[1]Statistically significant at P = 0.001.
Notes:
An "attempt" is defined to be the taking of the study drug and completion by the patient of the appropriate efficacy question on the patient questionnaire.
Analysis was done on average duration of erection for each patient during each period. For attempts which did not result in an erection, an duration of zero minutes was used in the statistical analysis.
All means, standard errors and P-values are from an ANOVA model, with effects for treatment, period, sequence, and patient within sequence.

TABLE 2

Duration of Erection
Results of Statistical Analysis of Average Durations
Based on All Attempts Where Erection Was Achieved

| Study Arm | Treatment Regimen | Number of Patients | Mean (Minutes) | Difference in Mean (Minutes) | Treatment Difference Standard Error |
|---|---|---|---|---|---|
| Apomorphine 6 mg | Drug | 70 | 13.96 | 4.925 | 0.959 |
|  | Placebo | 70 | 9.030 |  |  |
| Apomorphine 4 mg | Drug | 86 | 12.49 | 3.458 | 0.869 |
|  | Placebo | 86 | 9.028 |  |  |
| Apomorphine 2 mg | Drug | 83 | 10.82 | 1.811 | 0.978 |
|  | Placebo | 83 | 9.012 |  |  |

Notes:
An "attempt" is defined to be the taking of the study drug and completion by the patient of the appropriate efficacy question on the patient questionnaire.
Analysis was done on average duration of erection for each patient during each period. Attempts which did not result in an erection were not used in the statistical analysis.
All means and standard errors are from an ANOVA model with effects for treatment, period, sequence, and patient within sequence.

TABLE 3

Time to Erection
Kaplan-Meier Estimation of Median Time to Erection
Based on All Attempts

| Study Arm | Treatment Regimen | Number of Patients | Median (Minutes) | 95% Confidence Interval |
|---|---|---|---|---|
| Apomorphine 6 mg | Drug | 111 | 31.33 | 26.50–36.67 |
|  | Placebo | 111 | 47.50 | 43.75–52.86 |
| Apomorphine 4 mg | Drug | 131 | 36.00 | 32.50–42.27 |
|  | Placebo | 131 | 47.78 | 42.73–50.83 |
| Apomorphine 2 mg | Drug | 135 | 42.17 | 35.33–48.25 |
|  | Placebo | 135 | 50.00 | 44.86–54.38 |

Notes:
An "attempt" is defined to be the taking of the study drug and completion by the patient of the appropriate efficacy question on the patient questionnaire.
Analysis was done on average time until erection for each patient during each period. For attempts which did not result in an erection, a time until erection of 60 minutes was used.

TABLE 4

Time to Erection
Kaplan-Meier Estimation of Median Time to Erection
Based on Attempts When Erection Occurred

| Study Arm | Treatment Regimen | Number of Patients | Treatment Means | 95% Confidence Interval |
|---|---|---|---|---|
| Apomorphine 6 mg | Drug | 96 | 12.82 | 10.00–16.67 |
|  | Placebo | 82 | 11.67 | 10.00–14.00 |
| Apomorphine 4 mg | Drug | 110 | 12.61 | 10.00–16.00 |
|  | Placebo | 94 | 12.75 | 10.00–15.00 |
| Apomorphine 2 mg | Drug | 109 | 11.33 | 10.00–15.00 |
|  | Placebo | 92 | 12.42 | 10.30–15.00 |

Notes:
An "attempt" is defined to be the taking of the study drug and completion by the patient of the appropriate efficacy question on the patient questionnaire.
Analysis was done on average time until erection for each patient during each period.
Analysis is based on the first eight attempts.

illustrated in the graph depicted in FIG. 1, shows that the time required to reach maximum blood serum levels following subcutaneous delivery of apomorphine is approximately 15 minutes. However, as shown by the pharmacokinetic curves in FIG. 1, the maximum plasma concentrations following sub-lingual administration (the formulation used in the studies presented in Tables 1–4), was not reached until about 60 minutes following administration.

The data presented in Tables 3 and 4 show that the median time-to-erection is about 12 minutes, one-fifth the time required to reach maximum plasma concentrations following buccal administration. Since erections were observed in patients who had experienced difficulty achieving an erection in the absence of the drug, the data thus show a therapeutic effect beginning at 12 minutes following buccal administration. As shown by examination of FIG. 1, at that point in time, the drug has reached approximately one-fifth to one-fourth maximum blood serum levels, indicating that it is producing the desired effect at lower doses than initially believed necessary. In the period between administration of apomorphine and about 20 minutes following administration, the plasma concentration curves for all three doses tested (2 mg, 4 mg, and 6 mg) show similar profiles and interpolation of the data indicate that plasma apomorphine levels less than about 0.25 ng/mL are sufficient to cause a therapeutic effect. Production of plasma apomorphine concentrations generally ranging between about 0.02 ng/mL and 0.25 ng/mL are preferred for the method of this embodiment of the invention.

Thus the administration of a dose of apomorphine lower than that required for effective congestive arousal, but sufficient to increase genital blood flow is effective in extending the duration of erection and aids in normalizing the timing of sexual responses between the partners in intercourse.

Preferably, the dose administered to the patient in this embodiment of the invention is generally sufficient to produce mean plasma levels less than about 0.25 ng/mL, preferably in the range of about 0.02 ng/mL to about 0.25 ng/mL. These serum levels translate into doses generally ranging between about 0.02 mg to about 4 mg per dose, depending upon the formulation delivery system. In this embodiment of the invention, the mode of delivery of the drug is by acute administration; that is, in a dose administered on an as-needed basis in the time period immediately prior to sexual intercourse. The drug is preferably administered in a formulation which rapidly delivers the drug to the system and any method known to the practitioner of the pharmaceutical formulation arts which accomplishes this means may be used. For example, the drug may be rapidly delivered to the system by means of a liquid formulation applied sub-lingually; by a tablet, lozenge, or lollipop held in the mouth and absorbed buccally; by means of a suppository formulation administered intravaginally or rectally; by a powder, gel, or suspension, or an intra-nasal spray formulation.

The drug may also be administered in a sterile parenteral formulation by sub-cutaneous or intramuscular route, although sub-lingual, buccal, intra-nasal, and suppository formulations are preferred because of their greater ease of administration and the resulting greater potential for patient acceptance.

Depending upon the $T_{max}$ for a particular formulation, the drug is administered in the time period immediately prior to sexual intercourse, generally during the period between about 2 minutes and 120 minutes prior to sexual relations, preferably during the period between about 2 minutes and about 60 minutes prior to sexual relations.

In cases where the male sex partner suffers from sexual arousal disorder, or premature ejaculation, the drug is administered to the male, optionally with the co-administration of a low dose of androgen. In those instances where the female sex partner suffers from sexual arousal disorder, the drug is administered to the female, optionally with co-administration of a low dose of androgen.

By "co-administration" is meant 1) the administration of an androgen in a separate dosage form prior to administration of apomorphine, taking into account the particular pharmacokinetic profile of the androgen, and 2) the concomitant administration of the androgen and apomorphine in those cases where the pharmacokinetic profiles of the two drugs are similar. In concomitant administration of apomorphine and an androgen, the two drugs may be administered in a single dosage form, or may be administered at the same time in separate dosage forms.

In studies with female rats, response to apomorphine was observed when treated with low doses of testosterone. Animals treated with a combination of apomorphine and testosterone exhibited lordosis, genital grooming and other behaviors typically associated with sexual arousal. Suitable androgens for use in this embodiment of the invention include testosterone, dihydrotestosterone, and dehydroepiandrostenedione with testosterone being particularly preferred. When co-administration of an androgen is utilized in this method of the invention, the androgen is given is doses sufficient to produce plasma concentrations of about 1 nmol/L to 200 nmol/L.

As would be apparent to a person of ordinary skill in the art, it is reasonable to use the rat as a model for the affected vascular systems discussed herein such as, for example, the pudendal and penile vasculature, and to extend such studies to appropriate dosages and therapies for other subjects such as higher mammals and humans. As evidenced by Mordenti, "Man versus Beast: Pharmacokinetic Scaling in Mammals," *J. Pharm. Sci.*, 75: 1028–1040 (1986) and similar articles, dosage forms for animals such as, for example, rats can be and are widely used directly to establish dosage levels in therapeutic applications in higher mammals, including humans One of the present inventors contributed to the development of a bioassay of erectile function in a rat model at leastas early as 1991 (J.P.W. Heaton, et al., *J. Urol.*, 145: 1099–1102 (1991)), and also helped to demonstrate in comparative tests of erectile function in humans and rats, that the narrow effective dose window for an orally administered drug, apomorphine, is almost identical when suitably adjusted for the differences in body weight as taught by Mordenti, cited above (J.P.W. Heaton, et al., *Urology*, 45: 200–206 (1995)).

In an alternative embodiment of the present invention, a central nervous system sexual response initiator is administered chronically in a low maintenance dose to prevent, ameliorate, or reverse the damaging effects to the genital organs of extended periods of vasoconstriction. In this embodiment, the drug is administered on a repetitive or recurring scheduled basis over a long period of time, for example once daily, once weekly, or by a depot formulation such as a transdermal patch or biodegradeable intramuscular depot formulation.

The terms "chronic administration," or "maintenance dose" of a drug refer to the scheduled repetitive and regular administration of a drug to the patient over a long term.

The arteries in a normal flaccid penis and the unenlarged clitoris and labia are constricted. As a result, typical oxygen concentrations in such tissues are closer to venous rather than arterial oxygen levels. Periodic vasodilation of the penis and clitoris increase oxygen levels in these tissues. The higher oxygen levels supplied to tissue in the penis and clitoris, as well as vasodilation itself, shut down adverse metabolic processes such as TGF-P production and vascular wall remodeling which result in long term tissue damage. Thus under normal conditions, for example, a man has three to five erections per night in the body's self-regulating mechanism for vasodilating and oxygenating penile tissues.

For the purposes of this embodiment, it is not necessary that the drug be administered in an amount necessary to produce effective vasocongestive arousal, that is, in the male an erection sufficient for vaginal penetration. Typically a lower dose, sufficient for inducing vasodilation and increased blood flow to the genitalia is sufficient, generally daily doses sufficient to produce mean plasma concentrations of apomorphine of less than about 0.2 ng/mL, preferably in the range of about 0.02 ng/mL to about 0.2 ng/mL.

The maintenance of these low levels of serum concentration of the drug result in tumescence which is insufficient for intercourse, but produce sufficient vasodilation of the genital organs to combat the deleterious effects of restricted blood flow to the organs over time. Since the object of this embodiment of the invention is to obtain a low, steady-state blood serum level of the drug, the drug formulation need not be one which delivers the drug rapidly to the system, and typical formulations known in the art such as tablets, pills, lozenges, syrups, elixirs, suspensions and the like, such as those described below may be employed.

Pharmaceutical Formulations

Pharmaceutical compositions suitable for administration of the drug of the present invention comprise a therapeutically effective amount of the drug formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be administered to humans and other animals orally, rectally, parenterally, intravaginally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues. Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like. The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While there have been described and illustrated preferred embodiments of the present invention, one of ordinary skill in the art to which the invention pertains will recognize that various modifications may be made without departing from the scope of the invention as it is defined by the appended claims.

What is claimed is:

1. A method of treating premature ejaculation in a male mammal comprising administering to a male mammal in need of such treatment apomorphine or a pharmaceutically acceptable salt thereof in an amount sufficient to produce genital vasodilation but less than the amount required to produce effective vasocongestive arousal in said mammal, wherein said amount produces a plasma apomorphine concentration that is less than about 0.25 ng/mL.

2. The method of claim 1 wherein said male mammal is human.

3. The method of claim 2 wherein said apomorphine or pharmaceutically acceptable salt thereof is administered to said human during a period of between about two to about one-hundred-twenty minutes prior to sexual relations.

4. The method of claim 2 wherein said apomorphine or pharmaceutically acceptable salt thereof is administered to said human during a period of between about two to about sixty minutes prior to sexual relations.

5. The method of claim 2 wherein said apomorphine or pharmaceutically acceptable salt thereof is administered to said human in an amount sufficient to produce a plasma apomorphine concentration between about 0.02 ng/mL to about 0.25 ng/mL.

6. The method of claim 2 further comprising co-administration of an androgen.

7. The method of claim 6 wherein said androgen is selected from the group consisting of testosterone, dihydrotestosterone, and dehydroepi-androstenedione or a pharmaceutically acceptable salt thereof.

8. The method of claim 6 wherein said androgen is testosterone or a pharmaceutically acceptable salt thereof.

9. The method of claim 6 wherein said androgen is administered in an amount sufficient to produce a plasma androgen concentration between about 1 nmol/L to about 200 nmol/L.

10. The method of claim 2, wherein said apomorphine or pharmaceutically acceptable salt thereof is administered in an amount no more than about 6 mg.

11. The method of claim 2, wherein said apomorphine or pharmaceutically acceptable salt thereof is administered in an amount between about 0.02 mg to about 4 mg.

* * * * *